United States Patent
Ameer et al.

(10) Patent No.: US 6,699,470 B1
(45) Date of Patent: Mar. 2, 2004

(54) MESH-GEL CONSTRUCTS FOR CELL DELIVERY CONTAINING ENZYMES AND/OR ENZYME INHIBITORS TO CONTROL GEL DEGRADATION

(75) Inventors: Guillermo A. Ameer, Cambridge, MA (US); Robert S. Langer, Jr., Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/685,232

(22) Filed: Oct. 10, 2000

Related U.S. Application Data (60) Provisional application No. 60/158,769, filed on Oct. 12, 1999.

(51) Int. Cl.$^7$ .......................... A01N 63/00; A61F 2/00; C12N 11/04; C12N 5/06; C12N 5/08
(52) U.S. Cl. ................ 424/93.7; 424/423; 424/94.6; 435/177; 435/178; 435/182; 435/382; 435/395
(58) Field of Search ................ 435/177, 178, 435/180, 182, 382, 395; 424/423, 93.7, 94.6

(56) References Cited

U.S. PATENT DOCUMENTS

| | | | | | |
|---|---|---|---|---|---|
| 4,822,535 | A | * | 4/1989 | Ekman et al. | 264/4.3 |
| 4,837,379 | A | * | 6/1989 | Weinberg | 424/101 |
| 4,933,185 | A | * | 6/1990 | Wheatley et al. | 424/461 |
| 5,858,746 | A | * | 1/1999 | Hubbell et al. | 435/177 |
| 5,891,558 | A | * | 4/1999 | Bell et al. | 428/218 |
| 6,171,610 | B1 | * | 1/2001 | Vacanti et al. | 424/426 |
| 6,179,872 | B1 | * | 1/2001 | Bell et al. | 623/11.11 |
| 6,303,148 | B1 | * | 10/2001 | Hennink et al. | 424/489 |

* cited by examiner

*Primary Examiner*—David M. Naff
(74) *Attorney, Agent, or Firm*—Choate, Hall & Stewart (57) ABSTRACT

A cell delivery device is prepared comprising a controllable degradable gel phase, meshed within a polymer substrate for use in tissue-engineering. The gel phase comprises a degradable, natural or synthetic polymer, and includes a suspension of living cells. The polymer substrate comprises a biocompatible, degradable polymer, and may be synthetic or natural. Degradation of the gel phase may be controlled by enzyme activity or adjustment of gel phase physical properties. In one embodiment, the gel phase contains an enzyme and/or enzyme inhibitor to control degradation of the gel phase. The device is useful in tissue replacement and repair, and more particularly, in the repair of cartilage tissue.

55 Claims, 4 Drawing Sheets

MESH-GEL CONSTRUCTS FOR CELL DELIVERY CONTAINING ENZYMES AND/OR ENZYME INHIBITORS TO CONTROL GEL DEGRADATION

CROSS-REFERENCE TO RELATED APPLICATIONS

This application claims the benefit under 35 U.S.C. §119 (e) of U.S. Provisional Application No. 60/158,769 filed Oct. 12, 1999, the contents of which are herein incorporated by reference.

GOVERNMENT SUPPORT

This invention was made with government support under Grant Number R01-HL60435-01 awarded by the National Institutes of Health. The government has certain rights in the invention.

TECHNICAL FIELD

This invention relates generally to constructs used in tissue-engineering, and more particularly, to cell delivery constructs comprising a controllable degradable gel phase, meshed within a polymer substrate.

BACKGROUND ART

The field of tissue engineering has brought recent advances to the development of substitutes for donor tissue and improved methods of tissue repair. For example, by incorporating principles from the materials and biological sciences, constructs can now be designed to culture functional tissue in vitro for use in subsequent surgical implantation. See Langer & Vacanti, *Science* 260:920, 1993. These constructs often require a biocompatible support substrate to allow cells to be seeded and grown. By facilitating new tissue growth, these constructs offer a potential to ameliorate the limited supply of donor tissue and also, improve the resources available for repairing damaged and non-functional tissue.

The use of biocompatible, biodegradable, polymer substrates in tissue engineering constructs for seeding cells and growing new tissue, has been demonstrated by Langer and others using a variety of cell types. See Cima & Langer, *Chem. Eng. Prog.* 46, 1993; Takeda et al. *Transplantation Proc.* 27(1):635. The ability to incorporate different cell types greatly expands the versatility and applicability of such a device for use in various medical procedures. For example, scaffolds can be designed for applications ranging from the development of new muscle tissue, to the production of new arteries. See Niklason & Langer, *Transplant Immunology* 5:303, 1997. One example of a tissue engineering device is described in co-pending U.S. patent application Ser. No. 09/109,427 incorporated herein by reference. One embodiment of that invention is a device comprising a tubular substrate onto which muscle cells can be seeded and grown. The substrate is porous and comprised of a biodegradable polymer such as polyglycolic acid (PGA), polylactic acid (PLA), or poly lactic-co-glycolic acid (PLGA).

Although PGA scaffolds have a proven clinical history and offer certain advantages for use in tissue engineering, one major disadvantage is their lack of structural integrity immediately after the cell seeding process. In particular, the scaffold is "wet" with media and cells and remains very fragile for several weeks following seeding. However, implantation of cell scaffold units immediately after seeding facilitates quick integration of newly forming tissue with the existing tissue, thus improving the available methods of tissue engineering and repair.

Once the device is implanted, the seeded cells quickly begin to proliferate and release extracellular matrix molecules into the surrounding tissue. Therefore, it is also advantageous to have a device which can deliver a high concentration or density of cells. An example of a surgical application benefiting from immediate implantation of a freshly seeded scaffold is in the repair and replacement of cartilage tissue and specifically, the meniscal tissue of the knee.

Immediate implantation, however, requires that the device have the mechanical strength to withstand the implantation and suturing procedures directly after seeding the cells. Thus, the lack of integrity of conventional freshly seeded scaffolds, renders them inoperative for use in many medical and surgical applications.

One approach to develop a biocompatible device for delivering cells directly after seeding has been to entrap the cells within a gel. Although this method provides the ability to achieve high cell densities, it has two major limitations. First, most gels are similar to PGA meshes in that they lack mechanical strength. The gel entrapment device is not rigid and is therefore unable to withstand the implantation and suturing procedures. Attempts have been made to increase the strength of gel entrapment constructs (e.g. using gel solidification techniques such as photopolymerization), but these techniques are often harsh and result in damage or death to the cells. Second, gel entrapment constructs can hinder the immediate growth and proliferation of cells.

Without a means to control the degradation of the gel, the growth and matrix production of the cells is limited. The need therefore remains for a construct that can deliver a high concentration of cells, while retaining the structural integrity to withstand surgical procedures. The controllable degradable mesh-gel constructs of the present invention provide such a construct.

SUMMARY OF THE INVENTION

According to one aspect, the invention is a cell delivery construct comprising a gel phase meshed within a polymer substrate. The gel phase comprises a degradable, natural or synthetic polymer, and includes a suspension of living cells. The gel phase for example, could comprise polymerized fibrin, polymerized heparin, glycosaminoglycans, sugars, polysaccharides, self assembling peptides, or proteins. In a preferred embodiment, the gel phase comprises polymerized fibrin.

The polymer substrate comprises a biocompatible, degradable polymer, and may be synthetic or natural. A synthetic polymer may be selected from the group consisting of polyglycolic acid (PGA), polylactic acid (PLA), or poly lactic-co-glycolic acid (PLGA). In one embodiment, the polymer substrate comprises PGA. A natural polymer substrate may comprise collagen, alginic acid, cellulose, silk, starch, or pullalan. In one embodiment, the natural polymer comprises collagen.

The gel phase includes a suspension of living cells, whose selection depends on the desired application of the end construct. In one embodiment, the cells comprise cartilage tissue cells and have a final density of $5 \times 10^6$ cells/construct, the construct having a diameter of 0.5 cm, and a thickness of 0.2 cm.

In accordance with the invention, the cell delivery construct allows for the controlled degradation of the gel phase. The gel phase may be degraded with enzymes or by adjusting the physical properties of the gel phase, such as pH, temperature, or ionic equilibrium. Urokinase and heparinase are suitable enzymes for degrading a gel phase comprising polymerized fibrin and heparin respectively. In preferred embodiments, the enzyme is either solubilized in the gel phase or encapsulated within biocompatible, biodegradable, polymer microspheres.

In another embodiment, cross-linkers or inhibitors are solubilized in the gel phase or encapsulated within biocompatible, biodegradable, polymer microspheres. By hindering or slowing degradation, the cross-linkers or inhibitors provide further control over the degradation process.

According to another aspect, the invention is a method of producing a cell delivery construct. The steps of the method comprise providing a degradable gel phase including a suspension of living cells, providing a biocompatible, degradable, polymer substrate, and meshing the gel phase within the polymer substrate.

Other novel features will be set forth in the description which follows, or learned by practice of the invention to those skilled in the art.

DETAILED DESCRIPTION OF VARIOUS EMBODIMENTS

I. DEFINITIONS

The following terms are defined as applied to the written description and appended claims in order to provide a more precise understanding of the subject matter of the present invention.

Gel Phase As used herein, the term gel phase refers to a polymer having a fluidity at room temperature between that of a liquid and a solid. The gel phase comprises a biocompatible, degradable polymer with characteristics allowing for controllable degradation. The polymer comprising the gel phase may be synthetic or natural, and could for example be sugars or polysaccharides. In one embodiment of the invention, the gel phase comprises polymerized fibrin whose fluidity is controlled by adjusting the concentration of fibrinogen. Gelation time is controlled by thrombin concentration.

Gel Entrapment As used herein, the term gel entrapment refers to the stabilization of living cells within the gel phase without destroying cell viability. The selection of cell type is made with respect to the particular application in which the construct will be utilized. For example, the suspension of living cells may comprise smooth muscle cells, endothelial cells, epithelial cells, fibroblasts, myoblasts, bile duct cells, pancreatic islet cells, thyroid cells, parathyroid cells, adrenal cells, hypothalamic cells, pituitary cells, ovarian cells, testicular cells, salivary cells, chondrocytes, hepatocytes, enterocytes, nerve cells, cardiac cells or kidney cells. In a preferred embodiment, the cells comprise cartilage tissue cells (chondrocytes) for use in the repair of meniscal tissue. The cells are incorporated in aqueous form into a solution comprising the gel phase. The cells become stabilized within the gel phase after mixing with a second solution comprising the gel phase, which causes the gel phase to solidify.

Microspheres As used herein, the term microspheres refers to a "polymer cage" used to encapsulate molecules of interest. The microspheres are comprised of biocompatible, biodegradable, polymers, such as PGA, PLA, or PLGA. In accordance with preferred embodiments, the microspheres encapsulate enzymes, cross-linkers, or inhibitors and are introduced to the gel phase.

Cross-Linkers As used herein, the term cross-linkers refers to molecules having the ability to bind sites on the gel phase surface and link them together. The cross-linkers provide the gel phase with additional stability and integrity, furthering control over degradation. The cross-linkers may be peptides for example, which have a specific binding affinity for the gel phase. In one embodiment of the invention, Factor XIII is incorporated into the gel phase as a cross-linker.

Inhibitors As used herein, the term inhibitors refers to molecules which retard or hinder the degradation of the gel phase. The inhibitors can be introduced to the gel phase in soluble form, or entrapped within microspheres. The concentration of inhibitor can be selected to provide additional control of the degradation process. In one embodiment of the invention, the inhibitor may be an antiplasmin or an antiactivator, slowing degradation of a polymerized fibrin gel phase. Examples of antiplasmins which may be used in accordance with the present invention are: alpha-2-macroglobulin, alpha-1-antitrypsin, alpha-2-antiplasmin, antithrombin III, $C_1$ inactivator, inter-a-antitrypsin. Examples of antiactivators which may be used in accordance with the present invention are: tissue activation inhibitor, urokinase activation inhibitor, and $C_1$ inactivator.

Composite Construct As used herein, the term composite construct refers to a construct comprising a gel phase including at least one suspension of living cells, meshed within a polymer substrate.

Controlled Degradation As used herein, the term controlled degradation refers to the ability to control gel phase lysis by means that do not destroy the viability of the cells, or limit their proliferation. In one embodiment, enzymes are used to control degradation. In another embodiment, other means, including changing the temperature, pH, or ionic equilibrium of the gel phase may be used in accordance with the present invention. The incorporation of cross-linkers, and or inhibitors, provide additional control over gel phase degradation.

II. EMBODIMENTS OF THE INVENTION

A. Composite Construct

According to one aspect, the invention is a cell delivery construct comprising a gel phase, including a suspension of living cells, meshed within a polymer substrate. The gel phase comprises a biocompatible polymer, synthetic or natural, whose degradation can be controlled. The gel phase polymer may have an unique and identifiable site for cleavage by a specific enzyme, or physical properties which provide means to control degradation. In one embodiment for example, the gel phase may comprise polymerized fibrin whose degradation is controlled by the concentration of the enzyme urokinase.

The polymer substrate comprises a biocompatible, degradable polymer. The substrate may be comprised of any synthetic or natural polymer capable of degradation. For example, the synthetic polymer may be selected from the group consisting of polyglycolic acid (PGA), polylactic acid (PLA), or polylactic-co-glycolic (PLGA). In one embodiment the polymer substrate comprises PGA. The natural polymer substrate may comprise collagen, alginic acid, cellulose, silk, starch, or pullalan. In a preferred embodiment, the natural polymer comprises collagen. The polymer substrate may be biodegradable, or degradable upon appropriate enzymatic application.

Figure 1:
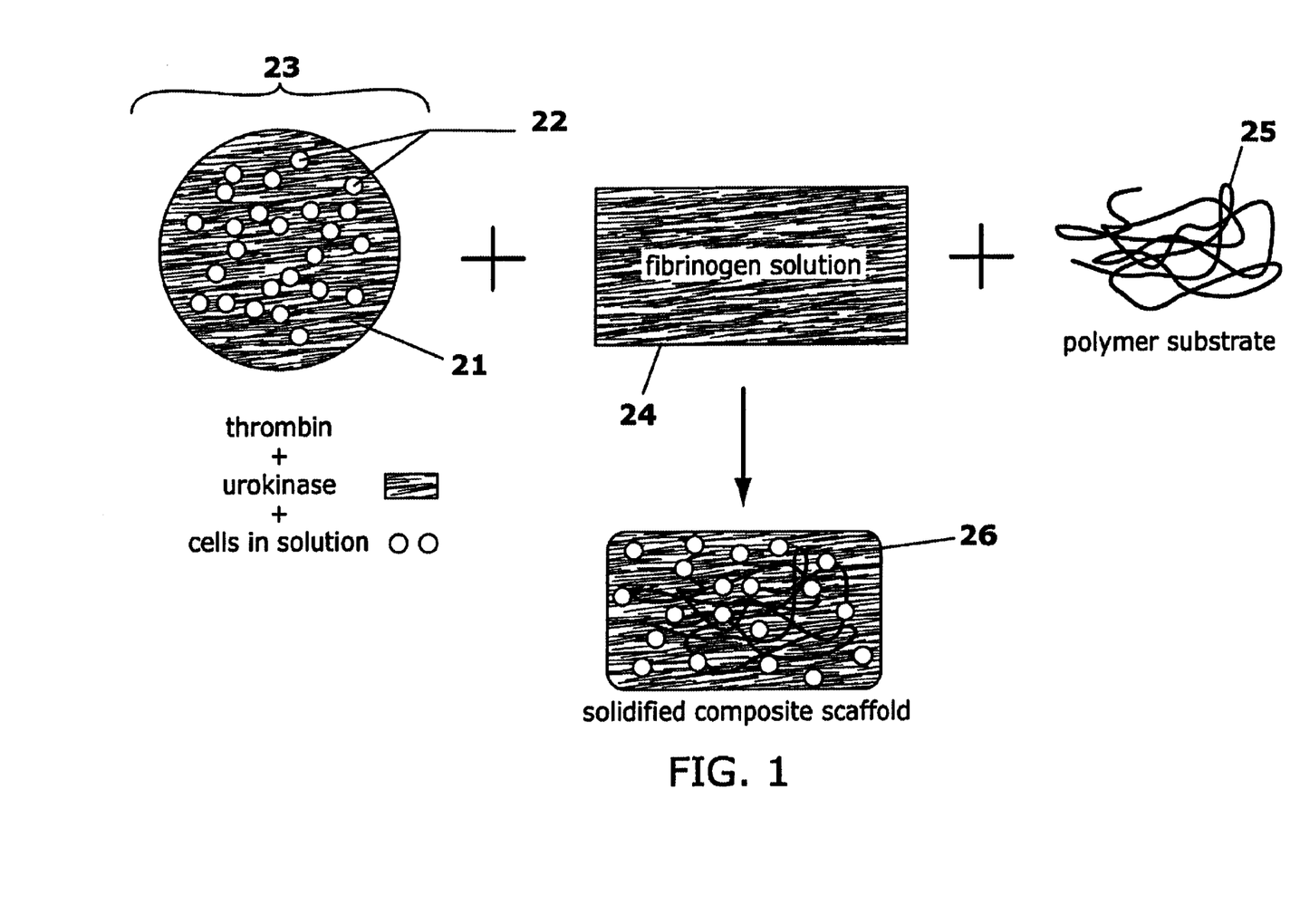
FIG. 1 is a schematic illustrating the components and assembly of the composite construct, in accordance with an embodiment of the invention.

FIG. 1 shows the components and assembly of the composite construct in accordance with an embodiment of the invention. A fibrin gel phase has two major components, fibrinogen and thrombin, which are prepared separately and mixed together to form a solidified gel (see Example 1). Referring now to FIG. 1, aqueous thrombin and urokinase (enzyme for activating the degradation of polymerized fibrin) are mixed in solution 21. Cells 22 are included in the gel phase by resuspending a cell pellet in solution 21. It is desirable to achieve high cell densities, and in one embodiment the final cell density is 5 million cells/construct, the construct having a diameter of 0.5 cm and a thickness of 0.2 cm.

The cells, urokinase, and thrombin 23 are then mixed with an aqueous fibrinogen solution 24 to comprise the gel phase. The fluidity of the gel phase may be controlled by adjusting the concentration of fibrinogen 24, with higher concentrations resulting in greater solidification. Similarly, the gelation time may be controlled by varying the concentration of thrombin, with higher concentrations resulting in faster gelation. The liquid gel phase is then meshed within a polymer substrate 25 (where gelation occurs) to comprise the composite construct 26. In this way, the cells are effectively localized and protected from surrounding shears. These steps can be repeated with different cell types thereby forming distinct layers.

The polymer substrate comprises a biocompatible, degradable polymer that may be synthetic or natural. For example, the synthetic polymer can comprise polylactic acid (PLA), polyglycolic acid (PGA), or a copolymer mixture thereof, poly-lactic-co-glycolic acid (PLGA). The natural polymer may comprise collagen, alginic acid, cellulose, silk, starch, or pullalan. The composite construct 26, comprised of a single or multiple layers of cells, is then ready for immediate implantation in the repair of cartilage tissue.

In accordance with the invention, the composite construct may be made impermeable to aqueous fluids, thus allowing for the direct perfusion of fluids within the construct. This may be of particular importance in the design of blood vessels or other conduits. In one embodiment, the fibrin gel phase is made impermeable by increasing the concentration of fibrinogen.

B. Controlled Degradation of Gel Phase

The ability to control gel phase degradation facilitates the expansion and infiltration of new cells within the existing tissue, while allowing the mechanical integrity of the construct to be maintained. In this way, the construct retains the strength to withstand the implantation and suturing procedures involved in repairing and engineering new growth of cartilage tissue. After these procedures have been successfully performed the gel phase is controllably degraded, allowing the suspension of living cells therein to expand and release extra-cellular matrix molecules into the surrounding tissue.

The degradation may be controlled by any suitable means that will not result in immediate cell death or destroy continued cell viability. For example, the gel phase may be degraded with enzymes or by adjusting the physical properties of the gel phase, such as, pH, temperature, or ionic equilibrium. Those skilled in the art will recognize that the selection of appropriate physical properties vary and that such selection should be made after considering the composition of the gel phase and the cell type incorporated therein. Degradation of the gel phase may also occur via the release of natural synthesis products from the entrapped cells.

According to one embodiment of the present invention, gel phase degradation is controlled by enzyme concentration. The enzyme may act by cleaving bonds specific to the polymer comprising the gel phase, or by activating a second enzyme capable of cleaving the bonds. The enzyme may be solubilized within the gel phase or encapsulated within biocompatible, biodegradable, polymer microspheres. The concentration of the enzyme controls the extent of degradation, and enzyme release over a pre-determined period controls the degradation rate.

Figure 2:
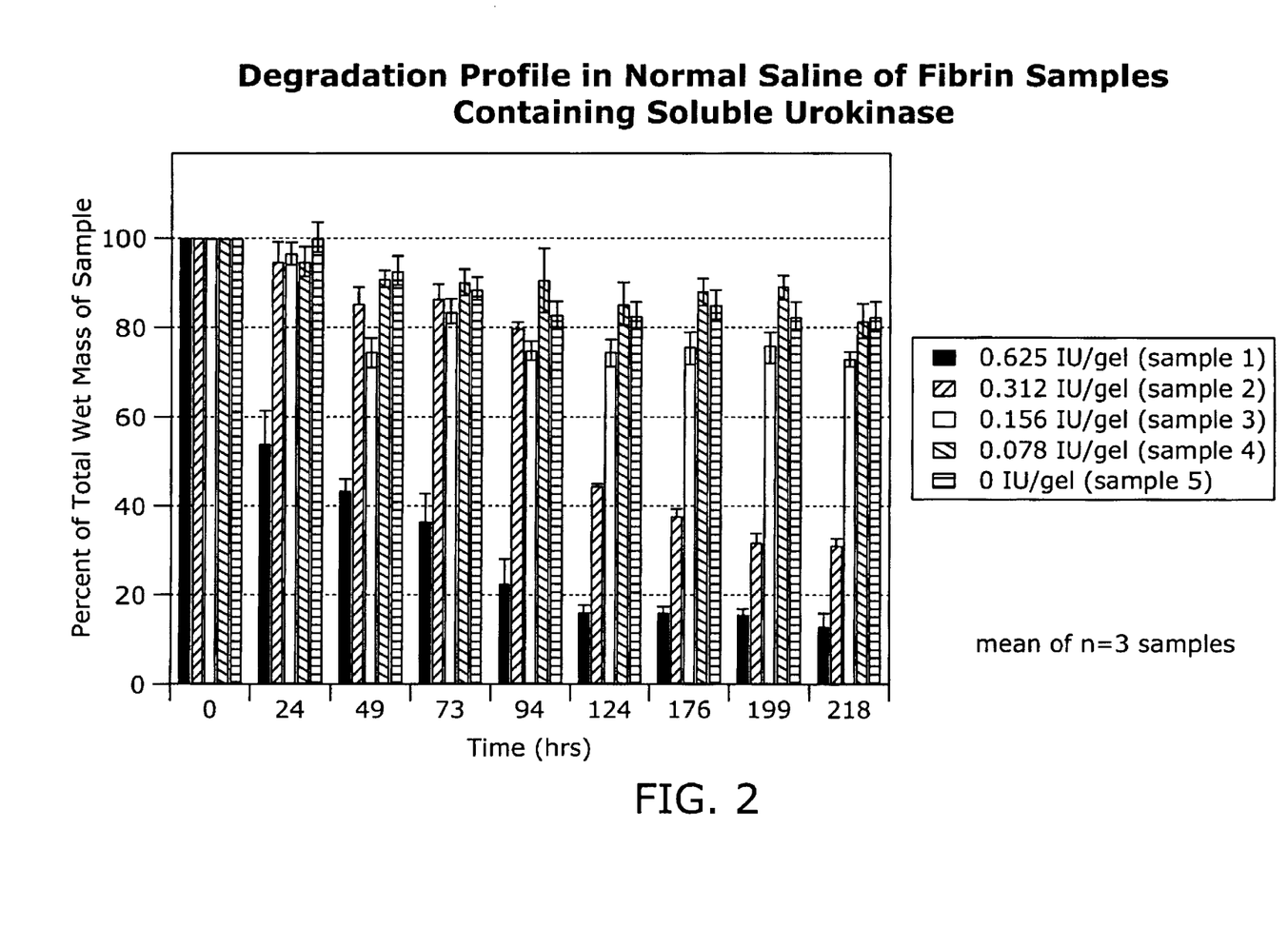
FIG. 2 is a graph demonstrating the relationship between the concentration of soluble urokinase and the degradation of a polymerized fibrin gel phase.

In one embodiment, the gel phase comprises polymerized fibrin and the enzyme urokinase is incorporated therein for controlling degradation. The concentration of urokinase may be selected to effect the extent of gel phase degradation. FIG. 2 is a graph demonstrating the relationship between the concentration of urokinase solubilized within a polymerized fibrin gel phase and the rate of fibrin gel degradation. The degradation experiments were performed in a normal saline solution to emulate biological conditions (e.g. biological pH).

Referring now to FIG. 2, time with units of hours is conveyed along the x-axis, and the percentage of total wet mass of the fibrin sample is conveyed along the y-axis. Each illustrated bar represents an average of three samples. The error bars represent the associated standard deviation. Sample 1 represents a polymerized fibrin gel phase including 0.625 international units of soluble urokinase. Sample 2 represents a polymerized fibrin gel phase including 0.312 international units of soluble urokinase. Sample 3 represents a polymerized fibrin gel phase including 0.156 international units of soluble urokinase. Sample 4 represents a polymerized fibrin gel phase including 0.078 international units of soluble urokinase. Sample 5 is a control representing a polymerized fibrin gel phase including no urokinase.

Figure 3:
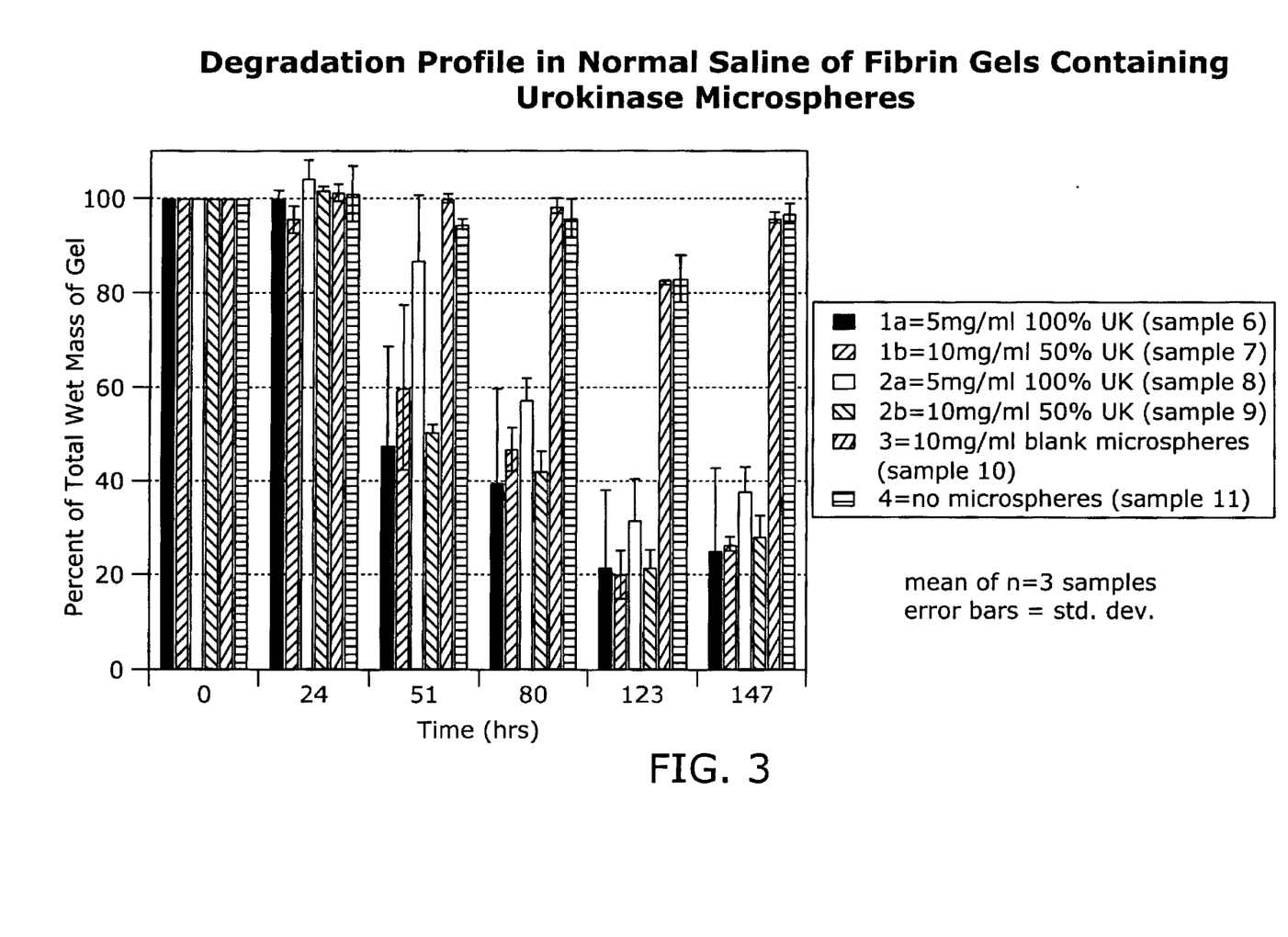
FIG. 3 is a graph demonstrating the relationship between the concentration of urokinase encapsulated within microspheres and the degradation of a polymerized fibrin gel phase.

In another embodiment, urokinase encapsulated within biocompatible, biodegradable polymer microspheres is incorporated into a fibrin gel phase to control degradation. FIG. 3 is a graph demonstrating the relationship between the concentration of urokinase encapsulated within microspheres and the rate of fibrin gel phase degradation. Time with units of hours is conveyed along the x-axis. The percentage of total wet mass of the fibrin gel is conveyed along the y-axis. The degradation experiments were performed in a normal saline solution to emulate biological conditions (e.g. biological pH). Each bar illustrated represents an average of three samples. The error bars represent the associated standard deviation.

Referring now to FIG. 3, sample 6 represents a polymerized fibrin gel phase sample including urokinase microspheres comprising 5 mg/ml of 100% urokinase. Sample 7 represents a polymerized fibrin gel phase including urokinase microspheres comprising 10 mg/ml of 100% urokinase (75% PLGA, 25% PLA). Sample 8 represents a polymerized fibrin gel phase including urokinase microspheres comprising 5 mg/ml of 100% urokinase (75% PLGA, 25% PLA). Sample 9 represents a polymerized fibrin gel phase including urokinase microspheres comprising 10 mg/ml of 100% urokinase. Sample 10 represents a polymerized fibrin gel phase comprising 10 mg/ml of microspheres which contain no urokinase. Sample 11 represents a polymerized fibrin gel phase including neither solubilized enzyme or enzyme encapsulated within microspheres.

Figure 4:
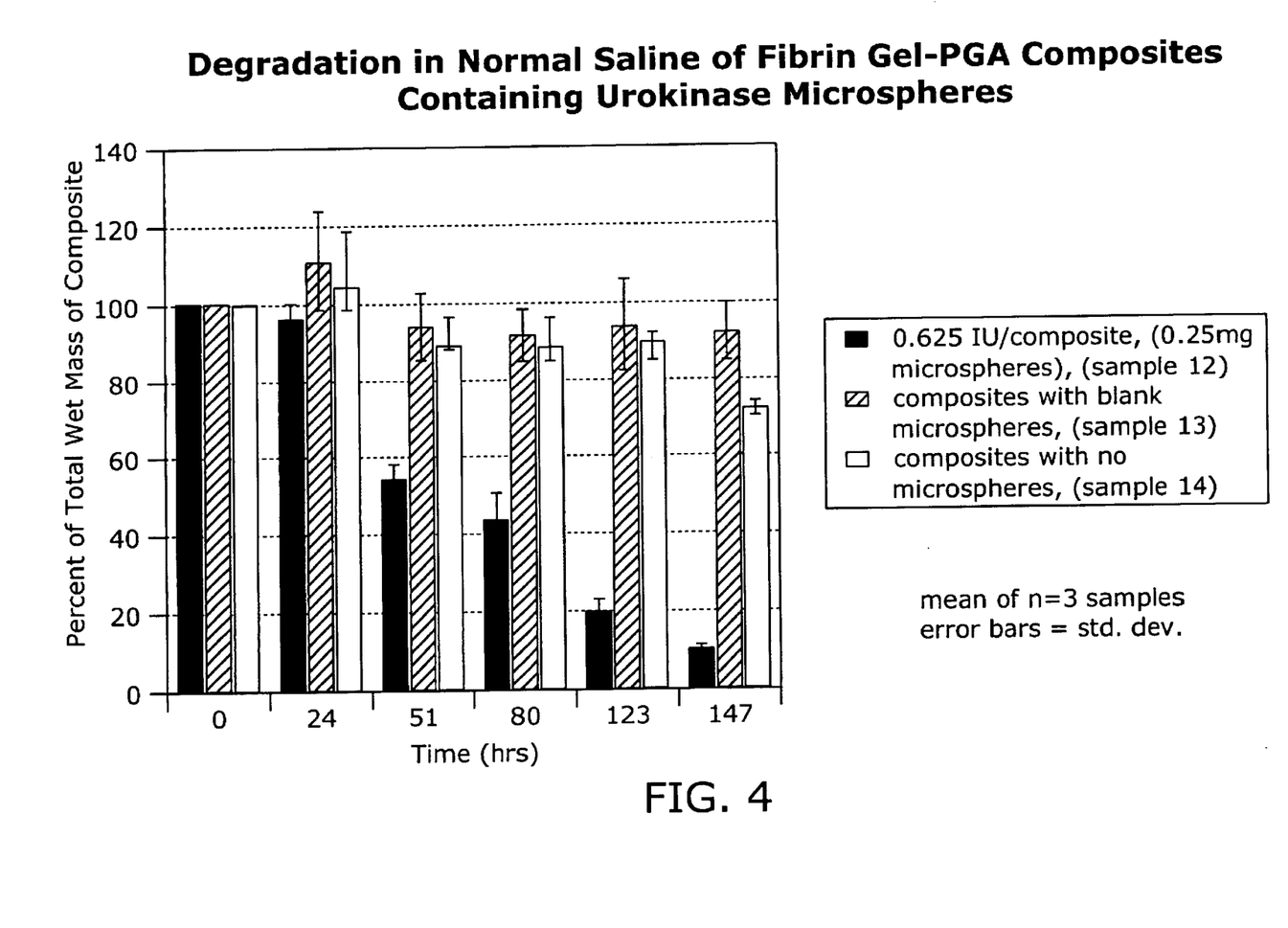
FIG. 4 is a graph demonstrating the relationship between the concentration of urokinase encapsulated within microspheres and the degradation of a composite construct.

FIG. 4 demonstrates the degradation of a composite construct using urokinase encapsulated within PLGA microspheres. Time with units of hours is conveyed along the x-axis. The percentage of total wet mass of the composite construct is conveyed along the y-axis. The degradation experiments were performed in a normal saline solution to emulate biological conditions (e.g. biological pH). Each bar illustrated represents an average of three samples. The error bars represent the associated standard deviation.

Referring now to FIG. 4, sample 12 represents a composite construct including 0.625 international units of urokinase (approximately 0.25 international units per mg of urokinase microspheres). Sample 13 represents a composite construct which includes blank microspheres. Sample 14 represents a composite construct which includes no microspheres.

In another embodiment, the gel phase comprises polymerized heparin and the enzyme heparinase I is used to control degradation.

Cross-linkers and or inhibitors may be incorporated into the gel phase to retard or hinder degradation. The incorporation of cross-linkers or inhibitors within the gel phase provides more control over the degradation process. The cross-linkers and inhibitors may be solubilized within the gel phase or encapsulated within biodegradable, polymer microspheres. In a preferred embodiment, the cross-linker comprises Factor XIII, and inhibitors are selected from the group including alpha-2-macroglobulin, alpha-1-antitrypsin, alpha-2-antiplasmin, antithrombin III, $C_1$ inactivator, inter-a-antitrypsin, tissue activation inhibitor, urokinase activation inhibitor and $C_1$ inactivator.

C. Cell Seeding

According to the invention, the gel phase includes a suspension of living cells. The selection of cells is based on the desired application for the final construct, and may, for example, comprise smooth muscle cells, endothelial cells, epithelial cells, fibroblasts, myoblasts, bile duct cells, pancreatic islet cells, thyroid cells, parathyroid cells, adrenal cells, hypothalamic cells, pituitary cells, ovarian cells, testicular cells, salivary cells, chondrocytes, hepatocytes, enterocytes, nerve cells, cardiac cells or kidney cells. In one embodiment, the cells comprise chondrocytes for use in the repair of meniscal tissue.

The cells are incorporated into the gel phase by a solidification process. The cells, in pellet form, are first resuspended into a solution comprising the gel phase. Mixing with a second solution then occurs. The mixing solution causes the gel phase to solidify, thus stabilizing the cells within the gel phase.

Providing a high seeding density of viable cells allows a greater number of cells to expand and release extracellular matrix molecules into the surrounding tissue. In one embodiment of the invention, the composite construct includes a high final density of cells. In a further embodiment the final cell density is at least $5 \times 10^6$ cells/construct, the construct having a diameter of 0.5 cm and a thickness of 0.2 cm.

III. EXAMPLES

Example 1

Preparation of Polymerized Fibrin gel Phase

Bovine plasma fibrinogen (containing up to 10% plasminogen) was obtained (Sigma, St. Louis, Mo.). An aqueous stock solution of normal saline was prepared by diluting NaCl to 0.9% in double distilled, purified water. A solution of fibrinogen was than prepared by dissolving 0.288 mg of the bovine plasma fibrinogen in 2.5 ml of normal saline. The resulting fibrinogen concentration was 115 mg/ml.

A stock solution containing 1000 units/ml of bovine plasma thrombin was obtained (Johnson & Johnson). The stock thrombin solution was than diluted 25 fold to yield a working thrombin solution having a final concentration of 40 units/ml. The dilution may be performed using either cell culture medium or 2 mM $CaCl_2$.

Aqueous urokinase was added to the working thrombin solution to obtain a urokinase activity of 3.1 units/ml (a 20 fold dilution of working solution). If urokinase microspheres are to be used, they are added to the working thrombin solution to yield a final activity of 12.5 units/ml.

The fibrinogen solution and the thrombin solution (containing urokinase) were then mixed together to comprise the fibrin gel phase.

Example 2

Preparation of Urokinase Microspheres

Urokinase stock solution having a concentration of 5,000 international units/ml was first obtained from Abott Laboratories (North Chicago, Ill.). A urokinase working solution having a concentration of 62.5 units/ml was prepared by diluting the stock solution 80 fold. Urokinase-PLGA microspheres were then prepared by double emulsion technique. First, 200 mg of PLGA powder (obtained from Boehringer and Ingelhem) was dissolved in 1 ml of methylene chloride obtained from Sigma ( St. Louis, Mo.). Then a volume of 100 $\mu$l of the stock urokinase solution (500 units total) was added to the solution of PLGA and methylene chloride.

The enzyme-polymer mixture was chilled on ice and sonicated on continuous mode for 5 seconds, creating a primary water in oil emulsion. The primary emulsion was homogenized for 1 minute at 9,500 rpm in an aqueous medium containing 2% PVA obtained from Sigma (St. Louis, Mo.). This step allows the urokinase to be encapsulated within the polymer.

The microspheres which formed were then stirred at room temperature for 3 hours and washed 3 times with deionized water by centrifugation, to remove excess methylene chloride. The formed microspheres had a mean wet diameter of 20 $\mu$m (vol. %) as measured by a coulter counter. The microspheres were then lyophilized for 48 hours and stored in a desiccator at room temperature prior to use. Approximately 200 mg of microspheres were obtained.

Example 3

Preparation of Composite Construct

Synthetic Polymer Substrate

The fibrin gel phase (described in example one) was added to a non-woven PGA mesh having a diameter of 0.5 cm and a thickness of 0.2 cm. The non-woven polyglycolic acid meshes (65 mg/ml density) were obtained from Albany International Research Co. (Mansfield, Mass.). The PGA polymer substrate was prepared as substantially described in co-pending U.S. application Ser. No. 09/109,427, incorporated herein by reference. The mesh was "massaged" gently to ensure thorough penetration of the gel. Visual observation and histological staining of sample cross sections confirmed gel penetration within the polymer fibers.

Natural Polymer Substrate

The fibrin gel phase (described in example one) may be added to a natural polymer mesh having a diameter of 0.5 cm and a thickness of 0.2 cm. The natural polymer mesh will comprise a natural polymer in a substrate form. The natural polymer may be selected from the group consisting of collagen, alginic acid, cellulose, silk, starch, or pullalan. If the polymer is not biodegradable, an enzyme appropriate for effecting degradation will be incorporated into the network. For example, cellulase will be incorporated into the substrate comprising cellulose, and pullalanase will be incorporated into the substrate comprising pullulan.

The mesh will be "massaged" gently to ensure thorough penetration of the gel. Visual observation and histological staining of sample cross sections will be used to confirm gel penetration within the polymer.

Example 4

Enzyme Degradation Experiments

To monitor the effect of the entrapped urokinase on the gel phase, separate degradation experiments were conducted with the fibrin gel and composite construct. The samples were placed in pre-weighed plates and monitored for weight changes (wet) over a period of 7 to 10 days. The fibrin gel samples were prepared as described in example 1 to form a 100 $\mu$l gel. The composite construct samples were prepared by mixing 50 $\mu$l of the working fibrinogen solution with 50 $\mu$l of the working thrombin and urokinase solution, and then adding the solution to a 1 cm²×2 mm thick PGA mesh. Three different types of experiments were performed: urokinase solubilized within a polymerized fibrin gel phase, urokinase-PLGA microspheres entrapped within fibrin gel, and urokinase-PLGA microspheres entrapped within the composite construct. Blank microspheres within the gel phase, and fibrin gel phase without urokinase, were used as controls.

The foregoing description of the preferred embodiments of the invention have been presented for purposes of illustration and description. It is not intended to be exhaustive or to limit the invention to the precise form disclosed. Obvious modifications or variations are possible in light of the above teachings. These embodiments were chosen and described to provide an illustration of the principles of the invention and its practical applications.

It should be appreciated by those skilled in the art that the specific embodiments disclosed above may readily be utilized as a basis for modifying or designing other methods or structures for carrying out the same purpose of the present invention. It should also be realized by those skilled in the art that such equivalent constructions do not depart from the spirit and scope of the invention as set forth in the appended claims.

What is claimed is:

1. A cell delivery construct comprising:
   a biocompatible, degradable, polymer substrate; and
   a gel phase meshed within the substrate, the gel phase comprising a controllably degradable polymer and including a suspension of living cells and further comprising a substance selected to control degradation of the gel phase, wherein the substance is selected from the group consisting of an enzyme capable of degrading the gel phase, an enzyme inhibitor and a combination thereof.

2. The construct of claim 1 wherein:
   the polymer substrate comprises a synthetic or natural polymer; and
   the gel phase comprises a synthetic or natural polymer.

3. The construct of claim 2 wherein:
   the synthetic polymer substrate is formed from a material selected from the group consisting of polyglycolic acid (PGA), polylactic acid (PLA), and poly lactic-co-glycolic acid (PLGA).

4. The construct of claim 2 wherein:
   the polymer substrate is formed from a material selected from the group consisting of collagen, alginic acid, cellulose, silk, starch, and pullalan.

5. The construct of claim 1 wherein:
   the gel phase polymer is formed from a material selected from the group consisting of sugars, polysaccharides, polymerized fibrin, polymerized heparin, glycosaminoglycans, proteins, agar, and self-assembling peptides.

6. The construct of claim 5 wherein:
   the gel phase includes said enzyme.

7. The construct of claim 1 wherein the living cells are selected from the group consisting of smooth muscle cells, endothelial cells, epithelial cells, fibroblasts, myoblasts, bile duct cells, pancreatic islet cells, thyroid cells, parathyroid cells, adrenal cells, hypothalamic cells, pituitary cells, ovarian cells, testicular cells, salivary cells, chondrocytes, hepatocytes, enterocytes, nerve cells, cardiac cells and kidney cells.

8. The construct of claim 7 wherein the cells comprise chondrocytes.

9. The construct of claim 1 wherein the cell density within the gel phase is at least $1 \times 10^6$ cells per 50 microliters of gel phase.

10. The construct of claim 1 wherein the cell density within the gel phase is at least $3 \times 10^6$ cells per 50 microliters of gel phase.

11. The construct of claim 1 wherein the cell density within the gel phase is at least $5 \times 10^6$ cells per 50 microliters of gel phase.

12. The construct of claim 6 wherein the gel phase polymer comprises polymerized fibrin, and the enzyme comprises urokinase.

13. The construct of claim 6 wherein the gel phase polymer comprises polymerized heparin, and the enzyme comprises heparinase.

14. The construct of claim 6 wherein the gel phase polymer comprises agar, and the enzyme comprises agarase.

15. The construct of claim 6 wherein the gel phase is impermeable to aqueous fluids.

16. The construct of claim 12 wherein the concentration of urokinase is in the range from 0–1.0 IU per 100 microliters of gel phase.

17. The construct of claim 6 wherein a cross-linker and/or said enzyme inhibitor is added to said gel phase; said cross-linker and/or enzyme inhibitor being capable of slowing degradation of said phase.

18. The construct of claim 17 wherein:

the cross-linker comprises Factor XIII; and the enzyme inhibitor is selected from the group consisting of alpha-2-macroglobulin, alpha-1-antitrypsin, alpha-2-antiplasmin, antithrombin III, $C_1$ inactivator, inter-a-antitrypsin, tissue activation inhibitor, urokinase activation inhibitor and $C_1$ inactivator.

19. The construct of claim 18 wherein:

the cross-linker and/or said enzyme inhibitor is entrapped within polymer microspheres within said gel phase.

20. The construct of claim 19 wherein:

the polymer microspheres are formed from a material selected from the group consisting of polyglycolic acid (PGA), polylactic acid (PLA), poly lactic-co-glycolic acid (PLGA) and polyanhydrides.

21. The construct of claim 1 wherein:

the gel phase polymer comprises polyethylene glycol.

22. The construct of claim 1 wherein:

the gel phase polymer comprises fibrin.

23. The construct of claim 6 wherein:

the enzyme is solubilized within said gel phase.

24. The construct of claim 6 wherein:

the enzyme is entrapped within biocompatible, degradable polymer microspheres.

25. The construct of claim 24 wherein:

the polymer microspheres are formed from a material selected from the group consisting of polyglycolic acid (PGA), polylactic acid (PLA), poly lactic-co-glycolic acid (PLGA), and polyanhydrides.

26. The construct of claim 1 wherein:

a cross-linker and/or said enzyme inhibitor is incorporated within the gel phase, the cross-linker and/or enzyme inhibitor being capable of slowing degradation of the gel phase.

27. The construct of claim 26 wherein:

the cross-linker and/or said enzyme inhibitor is solubilized within the gel phase or encapsulated within biocompatible, biodegradable microspheres.

28. The construct of claim 6, wherein the enzyme speeds degradation of the construct, thereby allowing increased expansion of the cells.

29. The construct of claim 6, wherein the construct is impermeable to aqueous fluids.

30. The cell delivery construct of claim 1, wherein the substance is said enzyme.

31. The cell delivery construct of claim 1, wherein the substance is said enzyme inhibitor.

32. A method for producing a cell delivery construct comprising the steps of:

providing a biocompatible, degradable, polymer substrate;

providing a gel phase comprising a controllably degradable polymer and including a suspension of living cells and further comprising a substance selected to control degradation of the gel phase, wherein the substance is selected from the group consisting of an enzyme capable of degrading the gel phase, an enzyme inhibitor and a combination thereof; and meshing the gel phase within the polymer substrate.

33. A method as in claim 32 wherein:

the polymer substrate comprises a synthetic or natural polymer; and the gel phase comprises a synthetic or natural polymer.

34. A method as in claim 33 wherein:

the polymer substrate is formed from a material selected from the group consisting of polyglycolic acid (PGA), polylactic acid (PLA), and poly lactic-co-glycolic acid (PLGA).

35. A method as in claim 33 wherein:

the polymer substrate is formed from a material selected from the group consisting of collagen, alginic acid, cellulose, silk, starch, and pullalan.

36. A method as in claim 33 wherein:

the gel phase polymer is formed from a material selected from the group consisting of sugars, polysaccharides, polymerized fibrin, polymerized heparin, glycosaminoglycans, proteins, agar, and self-assembling peptides.

37. A method as in claim 36 wherein:

the gel phase includes said enzyme.

38. A method as in claim 37 wherein the enzyme is selected from the group consisting of urokinase, heparinase, and agarase.

39. A method as in claims 38 wherein the enzyme has a concentration ranging from 1–1.0 IU per 100 microliters of gel phase.

40. A method as in claim 32 wherein the living cells are selected from the group consisting of smooth muscle cells, endothelial cells, epithelial cells, fibroblasts, myoblasts, bile duct cells, pancreatic islet cells, thyroid cells, parathyroid cells, adrenal cells, hypothalamic cells, pituitary cells, ovarian cells, testicular cells, salivary cells, chondrocytes, hepatocytes, enterocytes, nerve cells, cardiac cells and kidney cells.

41. A method as in claim 40 wherein the cells comprise chondrocytes.

42. The method of claim 32 wherein the cell concentration within the gel phase is at least $1\times10^6$ cells per 50 microliters of gel phase.

43. The method of claim 32 wherein the cell concentration within the gel phase is at least $1\times10^6$ cells per 50 microliters of gel phase.

44. The method of claim 32 wherein the cell concentration within the gel phase is at least $1\times10^6$ cells per 50 microliters of gel phase.

45. The method of claims 32 wherein:

a cross-linker and/or said enzyme inhibitor is added to the gel phase, the cross-linker and/or said enzyme inhibitor being capable of slowing degradation of the gel phase.

46. The method of claim 33 wherein:

the gel phase polymer comprises polyethylene glycol.

47. The method of claim 37 wherein:

the enzyme is solubilized in said phase.

48. The method of claim 37 wherein:

the enzyme is entrapped within biocompatible, degradable polymer microspheres.

49. The method of claim 48 wherein:

the polymer microspheres are formed from a material selected from the group consisting of polyglycolic acid (PGA), polylactic acid (PLA), poly lactic-glycolic acid (PLGA), and polyanhydrides.

50. The method of claim 37 wherein:

a cross-linker and/or said enzyme inhibitor is added to the gel phase, the cross-linker and/or enzyme inhibitor being capable of slowing degradation of the gel phase.

51. The method of claim 50 wherein:

the cross-linker comprises Factor XIII; and the enzyme inhibitor is selected from the group consisting of alpha-2-macroglobulin, alpha-1-antitrypsin, alpha-2-antiplasmin, antithrombin III $C_1$ inactivator, inter-alpha-antitrypsin, tissue activation inhibitor, urokinase activation inhibitor, and $C_1$ inactivator.

52. The method of claim 50 wherein:

the cross-linker and/or enzyme inhibitor is entrapped within polymer microspheres within the gel phase.

53. The method of claim 52 wherein:

the polymer microspheres are formed from a material selected from the group consisting of polyglycolic acid (PGA), polylactic acid (PLA), or polylactic-co-glycolic acid (PLGA) or polyanhydrides.

54. The method of claim 32, wherein the substance is said enzyme.

55. The method of claim 32, wherein the substance is said enzyme inhibitor.

* * * * *